United States Patent [19]
Hill et al.

[11] Patent Number: 6,006,134
[45] Date of Patent: Dec. 21, 1999

[54] METHOD AND DEVICE FOR ELECTRONICALLY CONTROLLING THE BEATING OF A HEART USING VENOUS ELECTRICAL STIMULATION OF NERVE FIBERS

[75] Inventors: Michael R. S. Hill, Minneapolis, Minn.; Kenneth R. Jonkman, Grand Rapids, Mich.

[73] Assignee: Medtronic, Inc., Minneapolis, Minn.

[21] Appl. No.: 09/070,506

[22] Filed: Apr. 30, 1998

[51] Int. Cl.[6] .............................. A61N 1/36; A61N 1/05
[52] U.S. Cl. ................................. 607/9; 607/118
[58] Field of Search .................. 607/5, 9, 118, 607/122

[56] References Cited

U.S. PATENT DOCUMENTS

| | | | |
|---|---|---|---|
| 5,014,698 | 5/1991 | Cohen . | |
| 5,056,519 | 10/1991 | Vince . | |
| 5,199,428 | 4/1993 | Obel et al. . | |
| 5,203,326 | 4/1993 | Collins . | |
| 5,243,980 | 9/1993 | Mehra . | |
| 5,330,507 | 7/1994 | Schwartz | 607/14 |
| 5,334,221 | 8/1994 | Bardy . | |
| 5,354,318 | 10/1994 | Taepke | 607/22 |
| 5,356,425 | 10/1994 | Bardy et al. . | |
| 5,507,784 | 4/1996 | Hill et al. . | |
| 5,549,655 | 8/1996 | Erickson | 607/42 |
| 5,578,061 | 11/1996 | Stroetmann et al. | 607/4 |
| 5,913,876 | 6/1999 | Taylor et al. | 607/2 |
| 5,916,239 | 6/1999 | Geddes et al. | 607/14 |

OTHER PUBLICATIONS

"Selective Stimulation of Parasympathetic Nerve Fibers to the Human Sinoatrial Node", Circulation, vol. 85, No. 4, Apr. 1992.

Pace Oct. 1992 vol. 15, No. 10, pt. 11, pp. 1543–1630 (on the use of nerve cuff stimulation of the vagal nerves).

Neural effects on Sinus Rate and Atrial Ventricular Conduction Produced by Electrical Stimulation from a Transvenous Electrode Catheter in the Canine Right Pulmonary Arty, by Cooper et al, Circulation research, vol. 46, No. 1, Jan. 1980, pp. 48–57.

*Primary Examiner*—Jeffrey P. Jastrzab
*Assistant Examiner*—Carl H. Layno
*Attorney, Agent, or Firm*—Reed A. Duthler; Harold R. Patton

[57] ABSTRACT

An electro-stimulation device includes a pair of electrodes for connection to at least one location in the body that affects or regulates the heartbeat. The electro-stimulation device both electrically arrests the heartbeat and stimulates the heartbeat. A pair of electrodes are provided for connection to at least one location in the body that affects or regulates the heartbeat. The pair of electrodes may be connected to an intravenous catheter for transvenous stimulation of the appropriate nerve. A first switch is connected between a power supply and the electrodes for selectively supplying current from the power supply to the electrodes to augment any natural stimuli to the heart and thereby stop the heart from beating. A second switch is connected between the power supply and the electrodes for selectively supplying current from the power supply to the electrodes to provide an artificial stimulus to initiate heartbeating. In another aspect, the invention is directed to a method for arresting the beat of a heart in a living body comprising the steps of connecting the pair of electrodes to at least one location in the body that affects or regulates the heartbeat and supplying an electrical current to the electrodes of sufficient amplitude and duration to arrest the heartbeat. The device may also serve to still the lungs by input to a respirator or by stimulation of the phrenic nerve during surgical procedures.

12 Claims, 10 Drawing Sheets

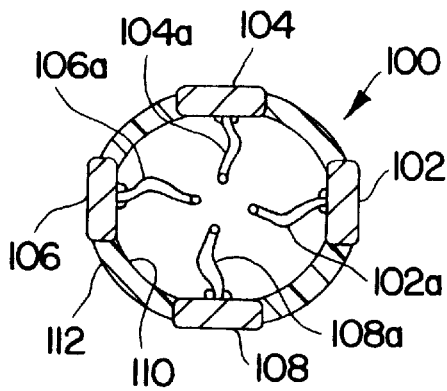
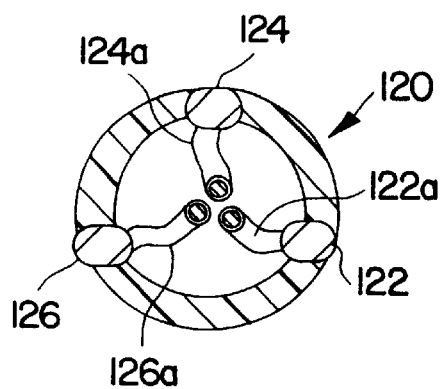
FIG. 7  FIG. 8
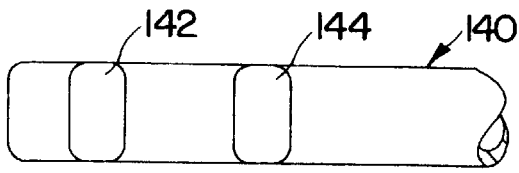
FIG. 9
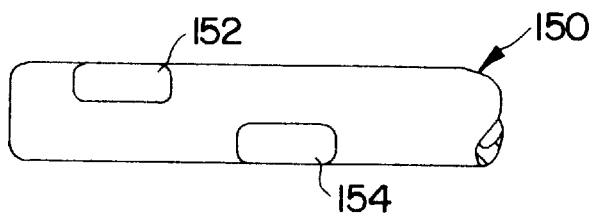
FIG. 10
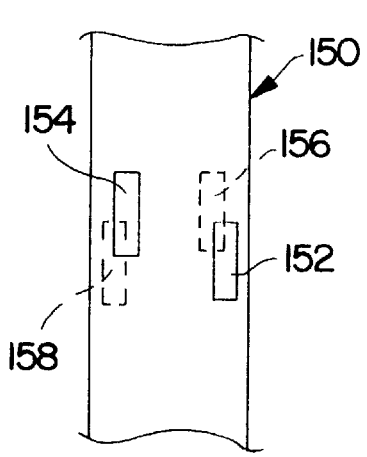
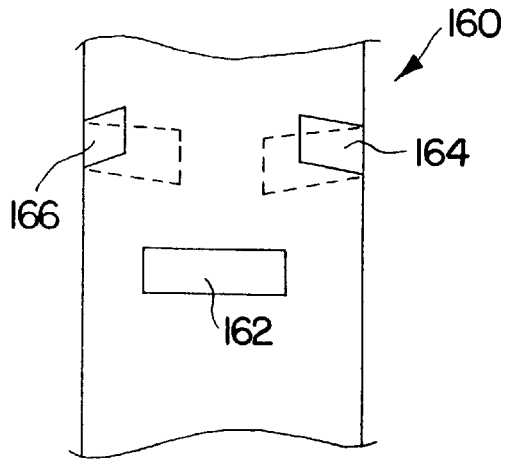
FIG. 11  FIG. 12

METHOD AND DEVICE FOR ELECTRONICALLY CONTROLLING THE BEATING OF A HEART USING VENOUS ELECTRICAL STIMULATION OF NERVE FIBERS

BACKGROUND OF THE INVENTION

1. Field of the Invention

This invention relates to methods and devices for controlling the operation of the human heart or other organs by means of electrical stimulation, and more particularly, to devices for electronically slowing or stopping the heart.

2. Description of the Related Art

In some surgical procedures, such as coronary bypass surgery, it is necessary to stop the heart from beating so that the surgeon can perform necessary techniques. The use of a cardioplegia solution to stop the heart from beating without rerouting the blood would permit the surgeon to accomplish the required task without interference from heart movement. However, this is not a viable approach, since the body needs a constant supply of oxygen. Thus, there exists a need to temporarily slow down or stop heart movement during minimally invasive CABG or other surgical procedures to permit the surgeon to accomplish the required task. In the context of treatment of the heart by means of implanted medical devices, such as pacemakers, defibrillators and drug dispensers, it is also sometimes beneficial to slow or temporarily stop the heart, either for diagnostic or therapeutic purposes.

It has been known in the past to stimulate the vagal nerves by invasively dissecting the major nerve bundle and placing a spiral or enveloping nerve-type cuff around the nerve bundle. The nerve fibers are then directly stimulated by electrical field to achieve reduction in epilepsy, heart rate slowing, and potential blood pressure changes. In a study entitled "Selective Stimulation of Parasympathetic Nerve Fibers to the Human Sinoatrial Node", Circulation, Vol. 85, No. 4, April 1992, it was reported that cardiac parasympathetic nerve fibers located in an epicardial fat pad at the margin of the right atrium, the superior vena cava, and the right pulmonary vein in humans could be electrically stimulated to affect the heart rate. Additional reference is found in PACE October 1992 Vol. 15, No. 10, pt. 11, pages 1543–1630 on the use of nerve cuff stimulation of the vagal nerves (left side) in humans for reduction of epilepsy and it's side-effects. Additional uses for electrical nerve stimulation have been disclosed for the prevention of arrhythmias, alteration of hemodynamics, stimulation of the hypoglossal nerve for sleep apnea, stimulation of the stomach, and control of the sphincter for bladder or colon evacuation.

Currently, only nerve cuff-type electrodes or impalement-type electrodes are used for nerve stimulation, other than in the spinal cord. These types of electrodes can potentially cause irreversible nerve damage due to swelling or direct mechanical damage of the nerve. The placement of these electrodes either around the nerve bundle or into the neural perineum also poses a significant risk. The electrode placement is usually performed through very invasive surgery which in and of itself produces a high risk to nerve damage, and would be self-defeating when performing minimally invasive surgery. However, it has been demonstrated that the paraympathetic nerve fibers associated with the heart can also be stimulated by means of electrodes located on transvenous leads, as in U.S. Pat. No. 5,243,980, issued to Mehra et al, U.S. Pat. No. 5,507,784, issued to Hill et al and U.S Pat. No. 5,356,425, issued to Bardy et al. The use of transvenous electrode leads to stimulate parasympathetic nerves associated with the heart is also discussed in the article "Neural effects on Sinus Rate and Atrial Ventricular Conduction Produced by Electrical Stimulation From a Transvenous Electrode Catheter in the Canine Right Pulmonary Artery, by Cooper et al., published in Circulation research, Vol. 46, No. 1, January 1980, pp. 48–57.

In conjunction with spinal cord stimulation, electrodes or electrode arrays located on pliant electrode pads are often employed. Recently, the ability to select from among various pairs of electrodes located on such electrode pads has been proposed to allow steering of the electrical field produced by the electrodes, as in U.S. Pat. No. 5,501,703, issued to Holsheimer, incorporated herein by reference in its entirety. Such electrode arrays offer additional possibilities to stimulate nerve fibers without direct and possibly damaging contact.

SUMMARY OF THE INVENTION

It is with these problems in mind that a new apparatus and method have been developed for electrically stimulating or destimulating certain nerves associated with the functioning of the heart or other organs which can be combined with certain surgical procedures or incorporated into implantable medical devices. According to one aspect of the invention, the invention is embodied in an electro-stimulation device includes at least two electrodes for connection to at least one location in the body that affects or regulates the heartbeat. At least one switch is connected between a power supply and the electrodes for selectively supplying current from the power supply to the electrodes to augment the natural stimuli to the heart in order to control the beating of the heart, and preferably to stop the heart from beating. Preferably, the switch is a foot switch operable by a surgeon to free a surgeon's hands during surgery.

According to another aspect of the invention, the at least two electrodes are connected to an intravenous catheter for transvenous stimulation/destimulation of the heartbeat.

According to another feature of the invention, an electro-stimulation device for both electrically destimulating and stimulating the heart includes a pair of electrodes for connection to at least one location in the body that affects or regulates the heartbeat. A first switch is connected between a power supply and the electrodes for selectively supplying current from the power supply to the electrodes to augment the natural stimuli to the heart and thereby stop the heart from beating. A second switch is connected between the power supply and the electrodes for selectively supplying current from the power supply to the electrodes to provide an artificial stimulus to initiate the heartbeat.

In a further aspect of the invention, a method for arresting the beat of a heart in a living body includes the process of connecting a pair of electrodes to at least one location in the body that affects or regulates the heartbeat and supplying an electrical current to the electrodes of sufficient amplitude and duration to arrest the heartbeat. According to one aspect of the invention, the step of supplying an electrical current to the electrodes includes supplying an alternating current.

In yet further aspects of the invention, the invention is embodied in an external or implantable device which employs electrodes located on transvenous leads located in veins adjacent nerve fibers to be stimulated. in these aspects of the invention, the leads preferably carry an array of electrodes from which pairs of electrodes can be chosen in order to direct the electrical field appropriately with respect to the desired nerve fibers.

It is to be noted that with regard to the effect of the delivered nerve or other stimulus pulses relative to the action of the heart the phrase "stimulate the heart" and its derivatives as used herein refer to the initiation of the heartbeat through the application of electricity, while the phrase "destimulate the heart" and its derivatives refer to stopping or arresting the heartbeat through the application of electricity.

BRIEF DESCRIPTION OF THE DRAWINGS

The invention will now be described with reference to the drawings in which:

FIG. 7 is a cross sectional view of a catheter and a set of electrodes positioned circumferentially around the catheter according to the invention;

FIG. 8 is a cross sectional view of a catheter and a set of electrodes positioned circumferentially around the catheter according to a second embodiment of the invention;

FIG. 9 is a side elevational view of a catheter with electrodes positioned axially along the catheter according to a third embodiment of the invention;

FIG. 10 is a side elevational view of a catheter with electrodes positioned axially along the catheter according to a fourth embodiment of the invention;

FIG. 11 is a top plan view of a catheter with electrodes positioned axially along the catheter according to a fifth embodiment of the invention;

FIG. 12 is a top plan view of a catheter with electrodes positioned axially and circumferentially along the catheter according to a sixth embodiment of the invention;

DETAILED DESCRIPTION OF THE PREFERRED EMBODIMENTS

Figure 1:
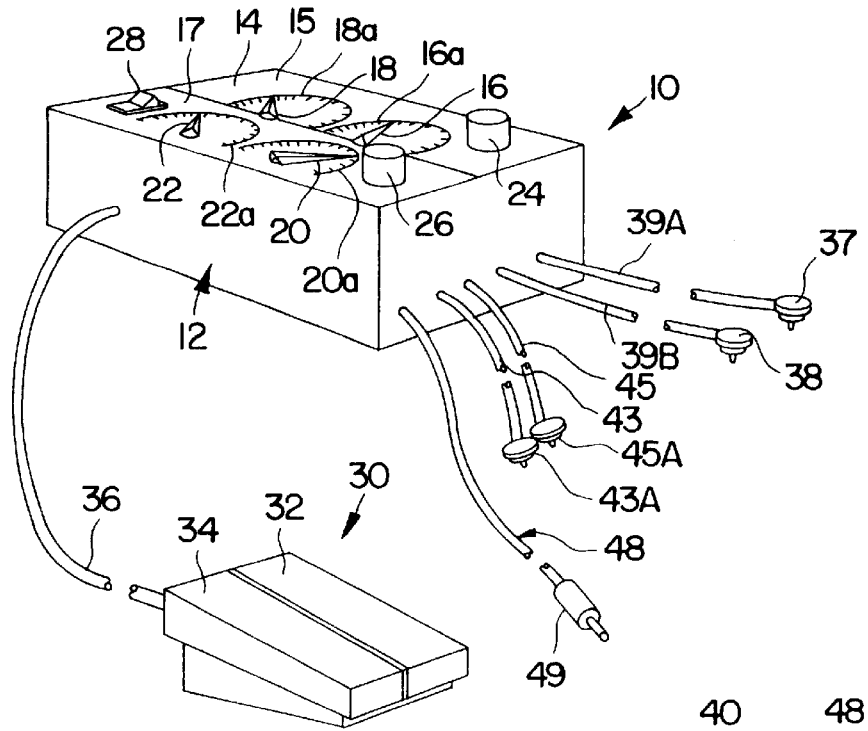
FIG. 1 is a perspective view of an electro-stimulation device according to the present invention.

Referring now to FIG. 1, a first embodiment of an electro-stimulation device 10 includes a housing 12 and a control panel 14 located on an upper surface of the housing 12. The control panel 14 is divided into a heart stimulation control area 15 and a heart destimulation control area 17. The stimulation control area 15 includes a rotary dial 16 and scale 16A for setting the amount of current that is passed to the heart, and a rotary dial 18 and scale 18A for setting the duration or frequency of cycles that the current is passed to the heart to start the heart beating. Likewise, the destimulation control area 17 includes a rotary dial 20 and scale 20A for setting the amount of current that is passed to the heart, and a rotary dial 22 and scale 22A for setting the duration that the current is passed to the heart to stop the heart from beating. Controls for regulating pulse width, pulse voltage, pulse phases and/or burst duration may also be added. A normally open stimulation switch 24 can be pressed to initiate heart stimulation while a normally open destimulation switch 26 can be pressed to initiate the heart destimulation. An on/off switch 28 can be used to turn the entire device off when not in use.

A foot pedal assembly 30 has a normally open heart stimulation foot switch 32 and a heart destimulation foot switch 34 that can be used as an alternative to switches 24, 26. The provision of a foot pedal assembly permits the surgeon to control when the heart stimulation and destimulation occurs while leaving the hands free to perform other procedures. This also permits the surgeon's hands to remain sterile since contact with the housing 12 or switches 26, 28 is avoided. The foot pedal assembly 30 is connected via cable 36 to an electronic control device 50 (FIG. 3) within the housing 12. An alternative to providing two different foot switches 32, 34 would be to provide a single foot switch which intermittently switches between stimulation and destimulation each time the switch is actuated. It is also contemplated that automatic stimulation could be provided after a preset time period or only if the device detects that the heart did not automatically restart.

A pair of electrodes 37, 38 are connected via a pair of leads 39A, 39B, respectively, to the electronic control device 50 for supplying electrical current to the heart during stimulation and destimulation. A second pair of electrodes 43A, 45A can also be connected via a pair of leads 43, 45, respectively, to the electronic control device 50 for supplying electrical current to the phrenic nerve to control breathing during heart stimulation and destimulation. A lead 48 having a connector 49 may be provided in addition to or alternatively of the phrenic nerve electrodes 43A, 43B. The connector 49 interfaces with a respirator (not shown) and, upon stimulation or destimulation of the heart, sends a logic signal to activate or deactivate the respirator.

Figure 2:
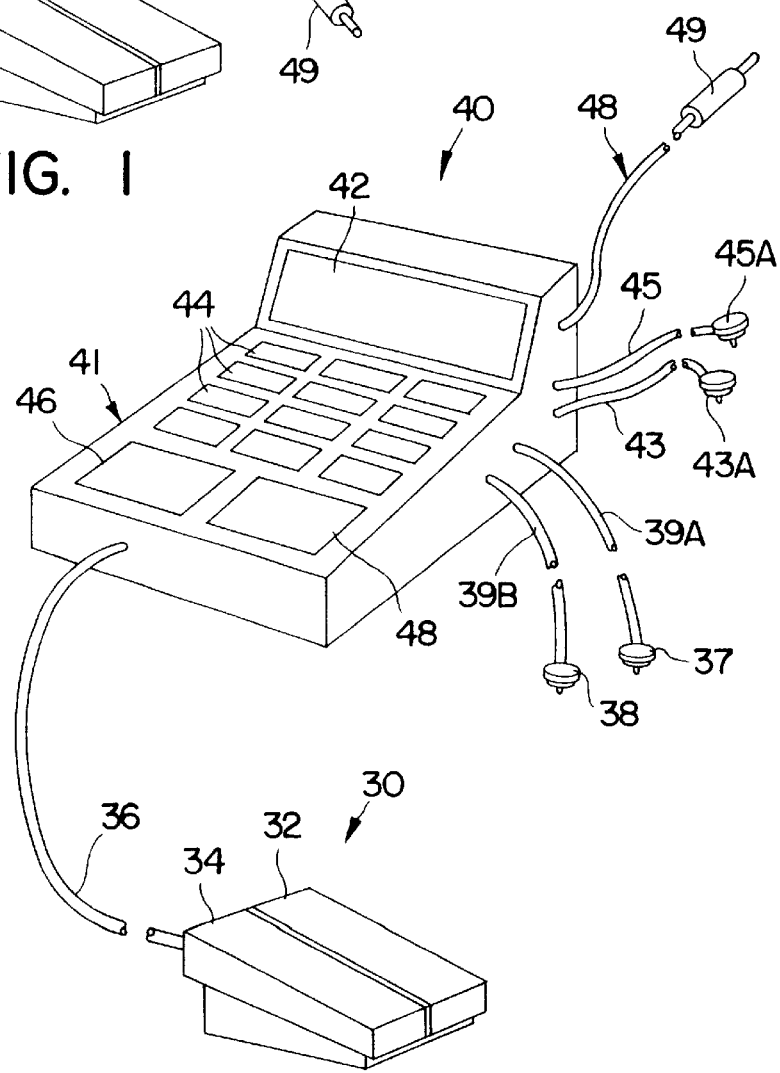
FIG. 2 is a perspective view of an electro-stimulation device according to a second embodiment of the present invention.

Referring now to FIG. 2, a second embodiment of an electro-stimulation device 40 according to a second embodiment is shown, wherein like parts from the previous embodiment are represented by like numerals. The electro-stimulation device 40 is microprocessor based and includes a housing 41 having a display 42, a plurality of numeric keys 44, a heart stimulation switch 46, and a heart destimulation switch 48. One of the keys 44 may be an on/off switch for supplying electrical power to the device 40. The device 40 prompts a user to enter the patient's age, height, weight, body temperature, etc., via the keys 44 to calculate the proper amount of electrical current and its duration necessary for proper heart stimulation and destimulation. In most instances, the amount of current and duration to stop the heart will typically be different than the amount of current and duration to start the heart, and will vary from one person to another depending on factors such as height, weight, body temperature, etc. In the embodiments of FIGS. 1 and 2, the current may be of the alternating, direct, or waveform type.

Figure 3:
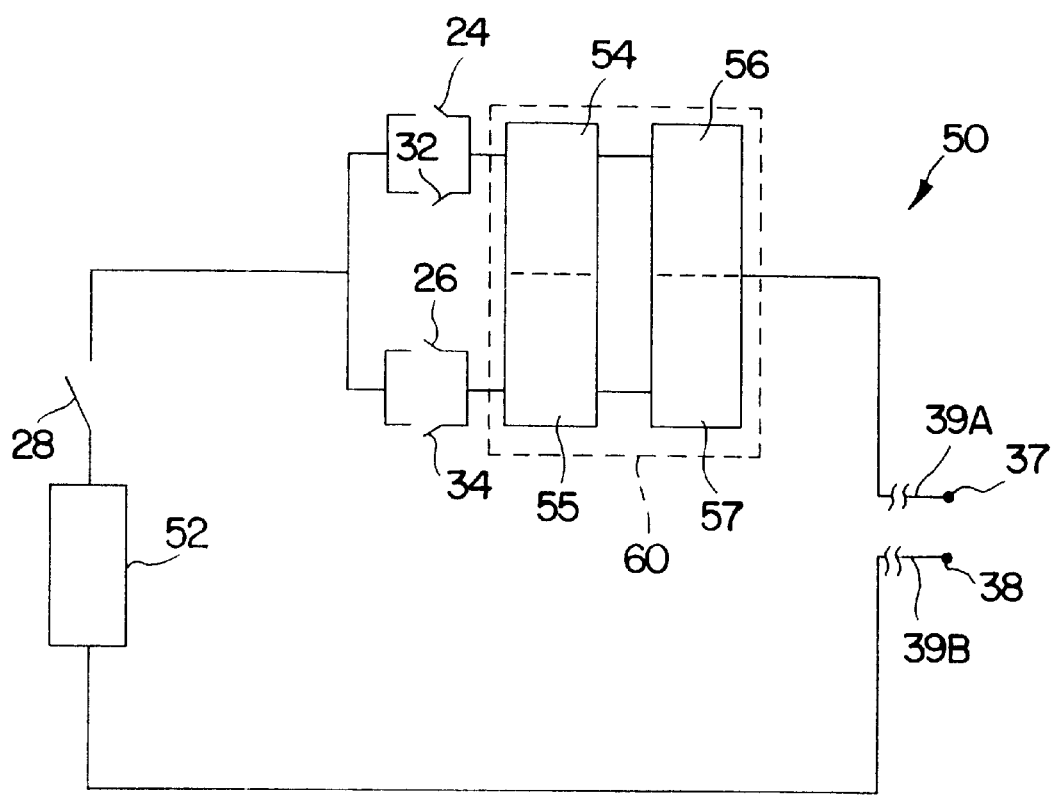
FIG. 3 is a schematic diagram of a circuit for use with the electro-stimulation device of FIGS. 1 and 2.

Referring now to FIG. 3, the electronic control device 50 for use with the electro-stimulator of FIGS. 1 and 2 includes a regulated power source 52, such as a battery and regulator, a stimulation timer circuit 54, a destimulation timer circuit 55, a stimulation power amplifier 56, and a destimulation power amplifier 57. The timer circuits and power amplifiers can be chosen from any of several well-known timers and amplifiers that can incorporate the dials 16, 18, 20, and 22. These dials may be of the variable resistive, capacitive, or pulse type to vary the timer frequency and power dissipation. Alternatively, input from the keys 44 stored in a microprocessor 60 (shown in dashed line) in the FIG. 2 embodiment can be used to vary the amplification and duration of the applied electrical current. The stimulation switch 24 and stimulation foot switch 32 on pedal assembly 30 are connected in parallel such that actuation of one or the other switch begins heart stimulation. Likewise, the destimulation switch 26 and stimulation foot switch 34 on pedal assembly 30 are connected in parallel such that the actuation of one or the other switch begins heart destimulation. Preferably, the switches are of the single-shot type that permit current to flow through the circuit for the amount of time set by the timers 54, 56, even when the switches are released. Alternatively, the switches may be of the type requiring manual positioning between the open and closed positions. In this alternative embodiment, the timers 54, 56 may provide an audible signal to indicate when the appropriate duration of electrical current application has been reached. The timers 54, 56 may also be eliminated. In this instance, the appropriate switch is manually closed until the surgeon visually observes that the heart has been properly stimulated or destimulated.

Figure 4:
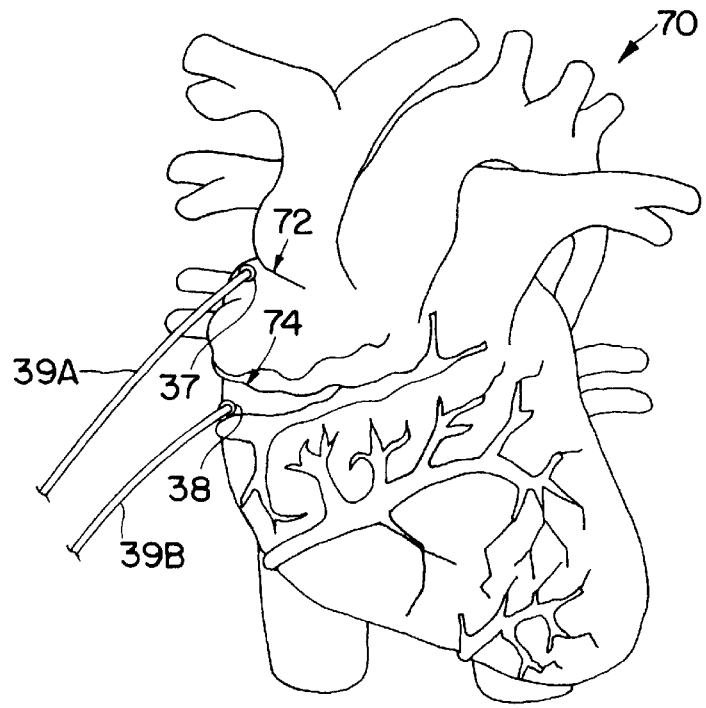
FIG. 4 is a diagrammatical view of a pair of electrodes of the electro-stimulation device attached to a pair of points on the heart.
Figure 5:
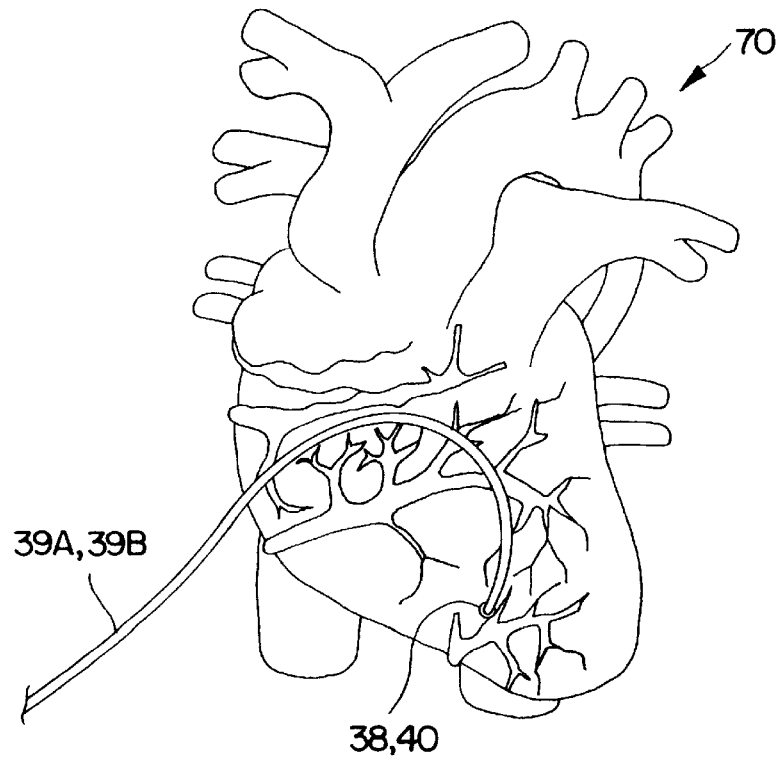
FIG. 5 is a diagrammatical view of a pair of electrodes of the electro-stimulation device attached to a single point on the heart.

With reference now to FIG. 4, the electrode 37 is connected to the sinoatrial region 72 of heart 70 while the electrode 38 is connected to the atrioventricular region 74 in a unipolar arrangement, while the electrodes 43A, 43B are connected to the phrenic nerve (not shown) or to other regions of the body or heart. The separate connection regions on the heart serve to alternatively stimulate and destimulate the heart. The electrode terminations may be of the type used in pacemakers, such as corkscrews, clips, pads, tines or barbs, needles, etc. The electrodes 37, 38 may both be connected to the ventricular wall as shown in FIG. 5 in a bipolar arrangement or at any position that a pacemaker is commonly connected to. The electrodes 43A, 43B may be connected in a bipolar arrangement to the vagus nerve or one of its cardiac branches. In the bipolar arrangement, the electrodes 37, 38 are placed near each other at a particular region for stimulating the heart while the electrodes 43A, 45A are placed near each other at a second region for destimulating the heart. The tissue between each pair of serves to close the circuit such that electrical current from the power source and amplifier passes through the tissue to cause stimulation or destimulation of the heart.

When the electrodes are connected to other locations besides the heart, a series of current pulses is passed long enough through the tissue to augment any recurring natural heartbeat stimuli to stop the heart from beating. It has been found that a continuous pulse train for 10–30 seconds using a constant current of 10–100 mA in conjunction with a constant pulse width of 0.01–0.5 msec. and a frequency between 6 Hz and 50 Hz applied to the epicardial parasympathetic nerves is sufficient to augment the recurring natural heartbeat stimuli to stop the heart. When the electrodes are connected directly to the heart, it is preferred that a burst pulse width of current be applied instead of a continuous pulse train. Once activity from the heart is sensed, a burst pulse width having the same current amplitude and frequency as in the constant pulse width is applied during the repolarization phase. Typically, the burst pulse time will be less than the continuous pulse train to stop the heart. Preferably, the burst pulse is programmable for different burst times, current amplitudes, and frequency. Upon cessation of heart destimulation, the natural heart beat stimuli will typically occur again automatically a short time thereafter. The separate heart stimulation leads, therefore, provide an added safety feature in the event that the heart does not automatically restart. In order to stimulate the heart, if required, a series of current pulses are passed through the tissue to initiate the natural heartbeat stimuli. These current pulses are similar to those used in pacemakers.

Figure 6:
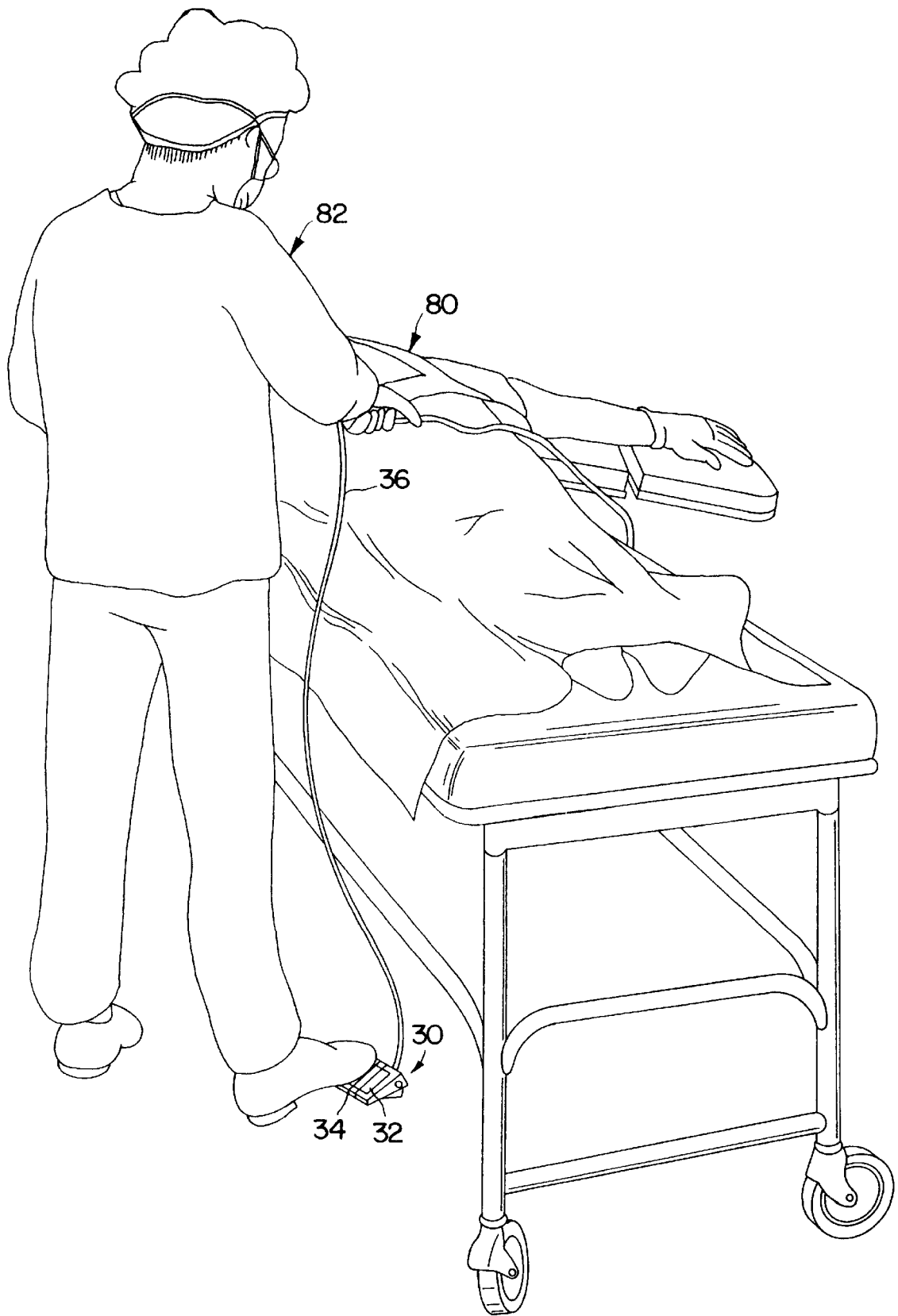
FIG. 6 shows operation of a foot pedal by a surgeon during heart electro-stimulation.

In use, the electrodes 37, 38 are secured at an appropriate position on the patient 80 (FIG. 6). During open surgery or minimally invasive surgery, as the surgeon 82 performs various steps such as cutting, stitching, etc., one of the foot switches 32, 34 is pressed to initiate or stop the heartbeat as required. For example, the surgeon may wish to stop the heartbeat while making one or a plurality of stitches where movement of the heart would normally be a hindrance. The heart may then be stimulated either naturally or artificially through the present device to beat for a predetermined time to permit blood flow throughout the body and then be destimulated or stopped again to continue stitching. If desired, the electrodes 43A, 45A may be connected to the phrenic nerve and/or the connector 49 may be attached to a respirator to still the lungs during the surgical procedure. When the electrodes are attached to the phrenic nerve, a continuous pulse train having the range of values as discussed previously is sufficient for controlling lung movement.

Referring now to FIG. 7, and according to a further embodiment, a set of four electrodes 102, 104, 106, and 108 are equally circumferentially spaced around a catheter 100. Each electrode 102–108 is embedded in and extends from an inner wall 110 to an outer wall 112 of the catheter 100. A separate insulated lead 102a, 104a, 106a, and 108a are each soldered or otherwise electrically connected to their respective electrode. The insulated leads extend through the catheter 100 and into the electronic control device 50. Any pair of electrodes can be accessed through extra switches in the control device 50 for supplying electrical current to the heart during stimulation and destimulation.

Referring now to FIG. 8, and according to a further embodiment, a set of three electrodes 122, 124 and 126 are equally circumferentially spaced around a catheter 120. Each electrode 122–126 is embedded in and extends from an inner wall 130 to an outer wall 132 of the catheter 120. A separate insulated lead 122a, 124a and 126a are each soldered or otherwise electrically connected to their respective electrode. As in the previous embodiment, the insulated leads extend through the catheter 100 and into the electronic control device 50. Any pair of electrodes can be accessed through extra switches in the control device 50 for supplying electrical current to the heart during stimulation and destimulation.

Although the catheters 100, 120 have been described with three or four electrodes, any number of electrodes may be provided, depending on the particular nerve stimulation application. For example, as shown in FIG. 9, two electrodes 142, 144 may be spaced axially on a catheter 140. The longitudinal centerline of each electrode 142, 144 extends perpendicularly to the axis of the catheter 140.

In FIG. 10, two electrodes 152, 154 are spaced axially and circumferentially from each other on the catheter 150. Their longitudinal centerlines extend parallel to the axis of the catheter. Two additional electrodes 156, 158 (shown in dashed line) may be provided on an opposite side of the catheter 150, as shown in FIG. 11.

In yet another embodiment, as shown in FIG. 12, a first electrode 162 is spaced axially and circumferentially from a pair of circumferentially electrodes 164, 166 on a catheter 160. Each of the electrodes 162–166 extends approximately 120° around the circumference of the catheter 160.

The catheters 100–160 as shown in FIGS. 7–12 are preferably of a small size to fit easily into the internal jugular vein, superior vena cava or other appropriate vessel adjacent to the desired nerve bundle. The internal jugular vein is next to the vagal nerve bundle, and thus presents an ideal path for the catheter when attempting to stimulate the vagal nerve. The human internal jugular vein is about 2 to 6 mm in diameter and tapers over an estimated length of about 15 cm. Hence, the use of a 7 F or smaller size catheter is contemplated. The electrodes are placed on the catheter in such a way that the amplitude required to stimulate the nerve fibers would have the correct field distribution. For an internal jugular vein of about 5 mm in diameter and a vagal nerve bundle of about 3 mm in diameter, and for an applied current of 10 mA with a frequency of 2–20 Hz, the spacing between the electrodes would need to be about 1–2 cm to achieve nerve stimulation. This spacing may vary depending on the size of the internal jugular vein and vagal nerve bundle, as well as the amount of applied current.

Figure 13:
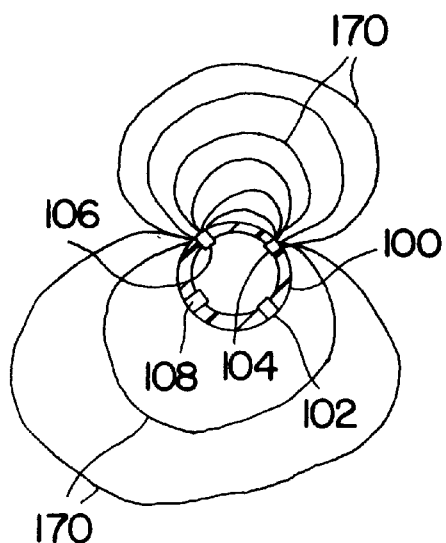
FIG. 13 is a cross sectional view similar to FIG. 8 showing the current density distribution between two of the electrodes.
Figure 14:
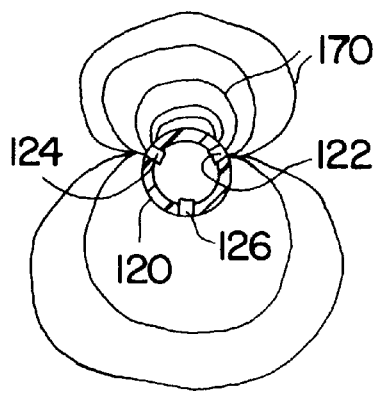
FIG. 14 is a cross sectional view similar to FIG. 7 showing the current density distribution between two of the electrodes.

Referring now to FIG. 13, electrodes 104, 106 of the catheter 100 are in contact with a nerve (not shown) and have been selected to apply a current thereto. The circumferential current density through the nerve tissue, as represented by lines 170, diminishes as the distance increases from the pair of activated electrodes. FIG. 14 shows a similar occurrence for the three-electrode embodiment of FIG. 8. Since the electrodes in this embodiment are spaced a greater distance than the electrodes from in the FIG. 7 embodiment, the current distribution is not as concentrated, and therefore produces a different neural stimulation.

Figure 15:
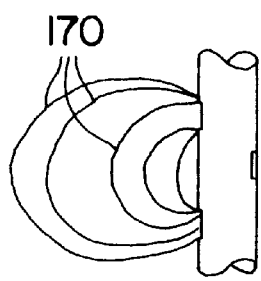
FIG. 15 is a top view of a catheter with electrodes positioned axially and circumferentially along the catheter and showing the current density distribution between two of the electrodes.

An axial current distribution may be required in addition to or in place of the circumferential distribution, as shown in FIG. 15, depending on the particular nerve stimulation desired. The axial current distribution is obtained by accessing a pair of axially spaced electrodes (FIG. 9) or a pair of axially and circumferentially spaced electrodes (FIGS. 10–12).

The preferred use of the electro-stimulation device would be a transvenous implementation through standard transvenous implantation techniques such as those used to implant pace/sense leads into the heart. For the method of transvenous vagal stimulation in laproscopic/endoscopic/minithorascopic surgical coronary artery bypass graft (CABG) procedures, the use of vagal nerve stimulation provides a reversible, quick acting (like an on/off switch) method for slowing the heart rate.

Although the foregoing description relates to the stimulation/destimulation of the heart during surgical procedures, it is not intended that the invention be limited thereto. The electro-stimulation device could be provided with two or more electrode-wielding catheters for use in multiple transvenous regions for the stimulation of different nerves. For example, a pair of catheters could be inserted into the internal jugular vein for stimulation of the right and left vagal nerve bundles. The right bundle could be used to elicit more specific heart effects and reduce heart rate and increase AV delay for antiarrhythmic and hemodynamic benefits; whereas the left bundle could be used to effect afferent vagal information and potentially reduce epileptic activity. An electrode-wielding catheter could be inserted into the very high internal jugular vein to stimulate the hypoglossal nerve and/or into the very low internal jugular vein or superior vena cava to stimulate the phrenic nerve for respiratory control. The stimulation of the phrenic nerve in conjunction with heart stimulation would insure that the blood is properly oxygenated during surgical procedures on the heart with intermittent heart destimulation. Likewise, catheters of the present invention could be inserted into the azygos or accessory hemizygous veins to stimulate the sympathetic nerves for increasing heart rate or altering DFT efficacy for antiarrhythmic and hemodynamic benefits. Other transvenous routes to nerve stimulation for functional purposes may also be applicable.

The electro-stimulation device may also have specificity for direction of neural stimulation in regards to the location of the vessel and the nerve bundle that is to be stimulated. For example, the phrenic nerve could be elicited on and off by a mere rotation of the transvenous catheter, depending on the location of the electrodes on the catheter and the resulting electric current density generated. In order to observe and control the amount of catheter rotation, a series of degree markings may be located on an outer circumference of the catheter at a position readily observable by the surgeon. Alternatively, the catheter may be associated with a rotary encoder to obtain a digital read-out of the amount of catheter rotation.

The electrodes of the intravenous catheters according to the present invention could also be used to manipulate the heart rate or hemodynamics in response to device sensors. In addition, in response to precursors of an arrhythmic event, the device may stimulate either the sympathetic or the parasympathetic individually or in combination to attempt to delay or prevent the event. Alternatively, current may be applied to different pairs of electrodes as discussed above.

Although the use of catheters having electrodes permanently mounted thereto for temporarily manipulating or stimulating nerves accessible through blood carrying vessels, it is to be understood that a more permanent nerve stimulation arrangement is possible by fixing electrodes onto the inside of the vessel adjacent to the nerve to be stimulated. Thus, this new device in its preferred embodiment eliminates the potential for direct nerve damage and reduces the invasiveness of the placement of the electrodes for direct neural stimulation in conjunction with implantable medical devices. Examples of how the present invention may be employed in the context of implantable medical devices are illustrated in FIGS. 16–19.

Figure 16:
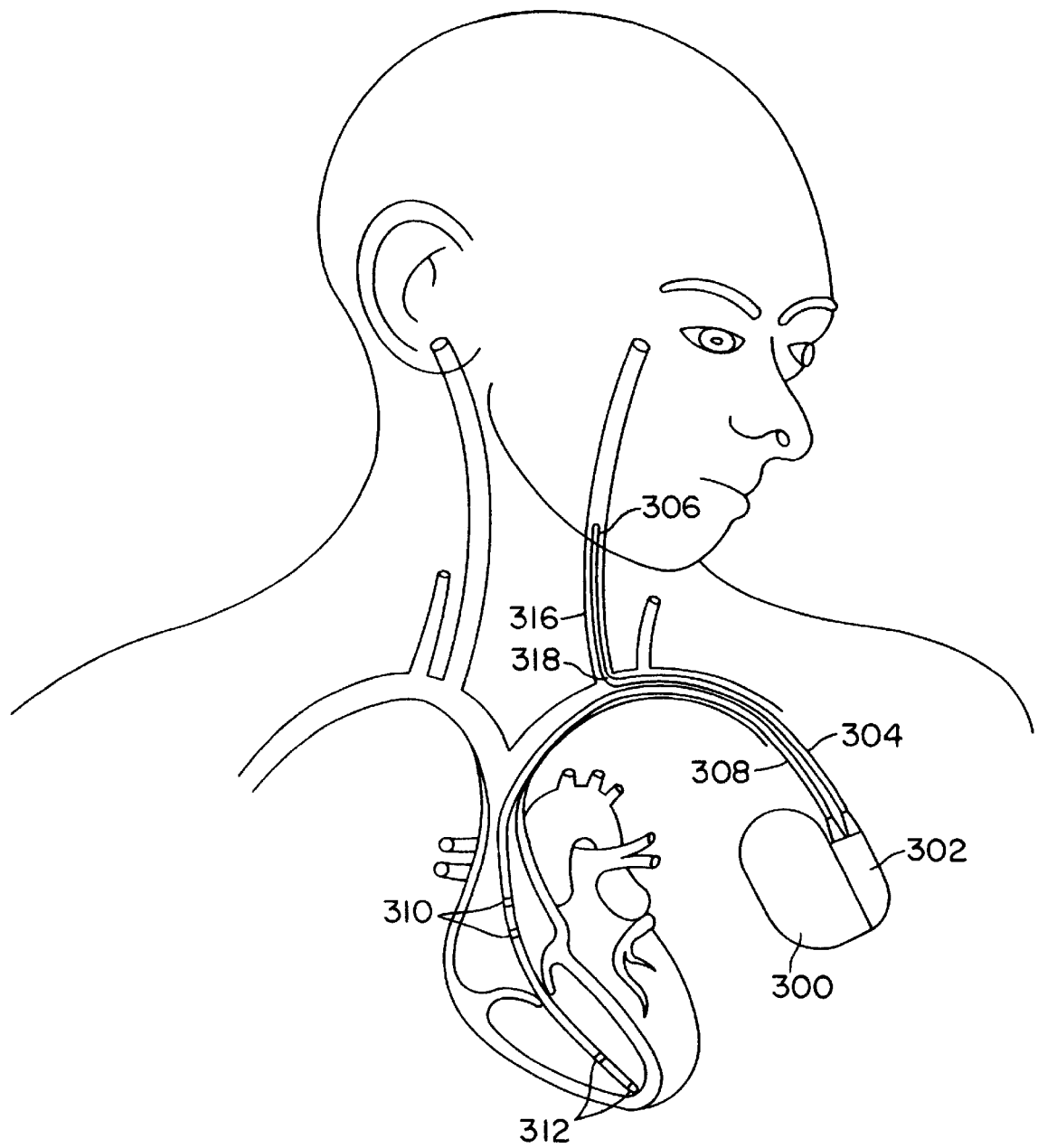
FIG. 16 illustrates an embodiment of the invention as employed with an implantable cardiac pacemaker which also stimulates the vagal nerve to treat arrhythmias and/or angina.

FIG. 16 illustrates an embodiment of the present invention employing a permanently implantable cardiac pacemaker 300 coupled to an electrode lead 304 used to stimulate the vagal nerve in accordance with the present invention. The pacemaker is also provided with a second electrical lead 308, which, like electrical lead 304 is coupled to the circuitry within the housing of pacemaker 300 by means of a connector block 302. Pacemaker 300 includes therein both a dual chamber cardiac pacemaker and an implantable nerve stimulator, and may correspond to that illustrated in U.S. Pat. No. 5,334,221 issued to Bardy; U.S. Pat. No. 5,330,507 issued to Schwartz or U.S. Pat. No. 5,199,428 issued to Obel et al, all of which are incorporated herein by reference in their entireties.

Electrode lead 304 has an array of electrodes as illustrated in FIGS. 7–15, discussed above, located at or adjacent its distal end 306 which is positioned within the internal jugular vein 316, with electrodes chosen to direct the stimulation pulses provided by the electrodes to the vagal nerve in order to slow heart rate. The second electrode lead 308 carries a pair of electrodes 310 for sensing depolarizations of the atrium of the patient's heart and a pair of electrodes 312 for sensing and pacing the ventricle of the patient's heart. As described in the above cited patents, the electrodes on lead 304 may be employed to slow the patients heart rhythm in order to prevent or treat detected arrhythmias, ischemia, angina or other problems. The electrodes 310 and 312 may be employed to sense the rate of the heart and to ensure that the heart is beating at an adequate rate, preventing overstimulation of the vagal nerve from causing the heart to drop below a base heart rate determined either as a fixed parameter or as a function of an indwelling activity sensor within pacemaker 300. Electrode lead 304 may be formed with a bend 318, preformed into the body of the lead a distance from the electrode array the distal end of the lead 306 to position it appropriately for vagal nerve stimulation. The lead may be inserted and positioned generally according to the procedure disclosed in U.S. Pat. No. 5,354,318 issued to Taepke, describing a similarly located and configured lead, also incorporated herein by reference in its entirety.

Figure 17:
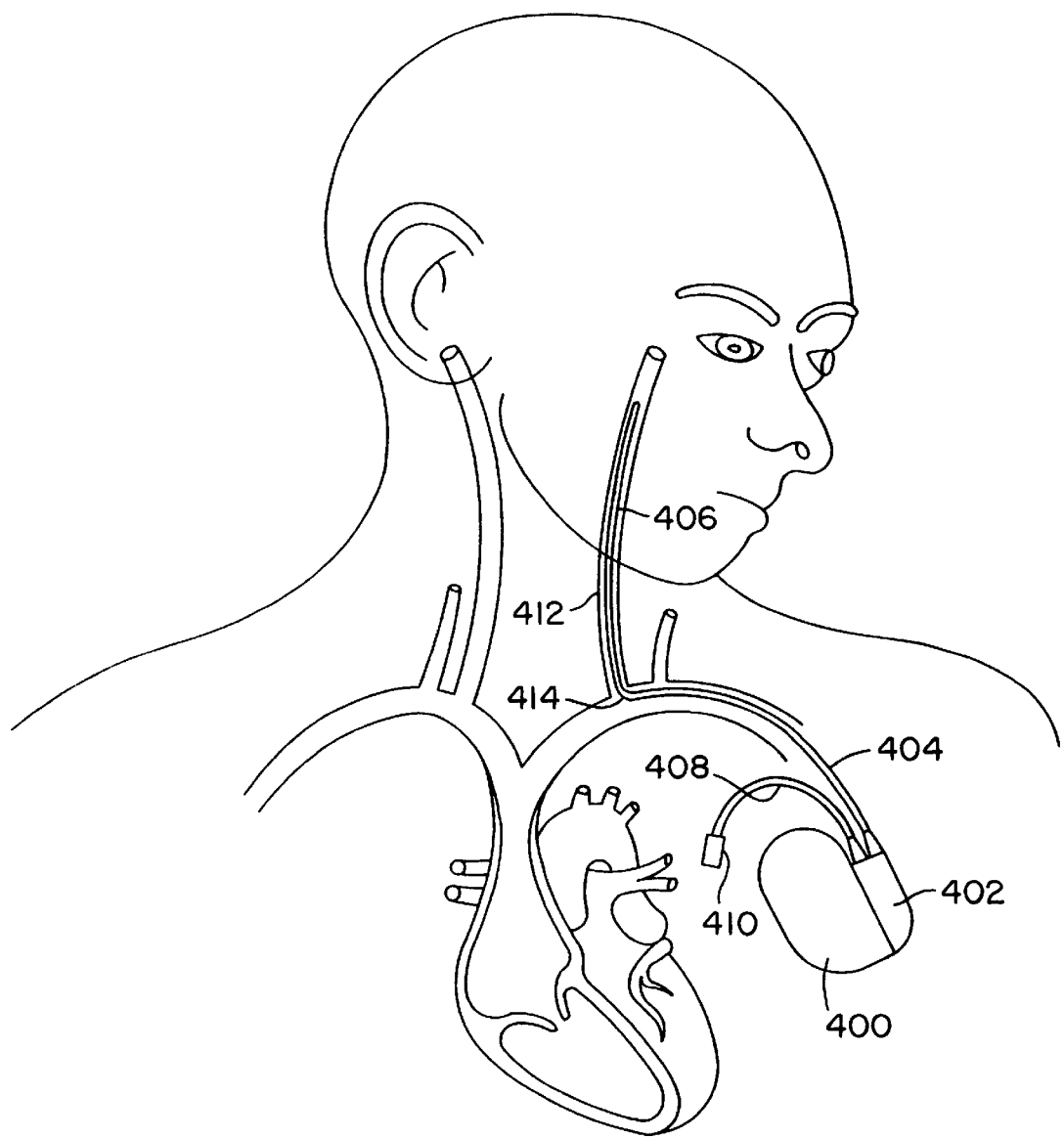
FIG. 17 illustrates the present invention in an embodiment including an upper airway stimulator in which stimulation of the hypoglossal nerve is employed to treat obstructive sleep apnea.

FIG. 17 illustrates an embodiment of the invention in which an implanted stimulator 400 is used in conjunction with an electrode lead according to the present invention to stimulate the hypoglossal nerve to treat obstructive sleep apnea. The pulse generator may correspond to that disclosed in U.S. Pat. No. 5,549,655 issued to Erickson and incorporated herein by reference in its entirety. The stimulator 400 is provided with a first electrode lead 404 which carries adjacent its distal end 406 an array of electrodes as described in FIGS. 7–15, discussed above. The lead is located relatively higher up within the internal jugular artery than the electrode array in FIG. 16 and is directed to stimulate the hypoglossal nerve by selection of appropriate electrodes as described above. Like the lead 304 described in FIG. 16, lead 404 may optionally be provided with a preformed bend 414, an appropriate distance from the location of the electrode array the distal end 406 of the catheter to position it in appropriate position and orientation to stimulate the hypoglossal nerve. The lead, like lead 304 in FIG. 16, may be inserted according to the procedure described in U.S. Pat. No. 5,354,318 issued to Taepke. The pulse generator 400 is additionally provided with a second lead 408 which carries a pressure sensor 410 which is used to synchronize delivery of hypoglossal nerve stimulus pulses to the detected inspiratory phase of the respiration cycle as described in the above cited Erickson patent.

Figure 18:
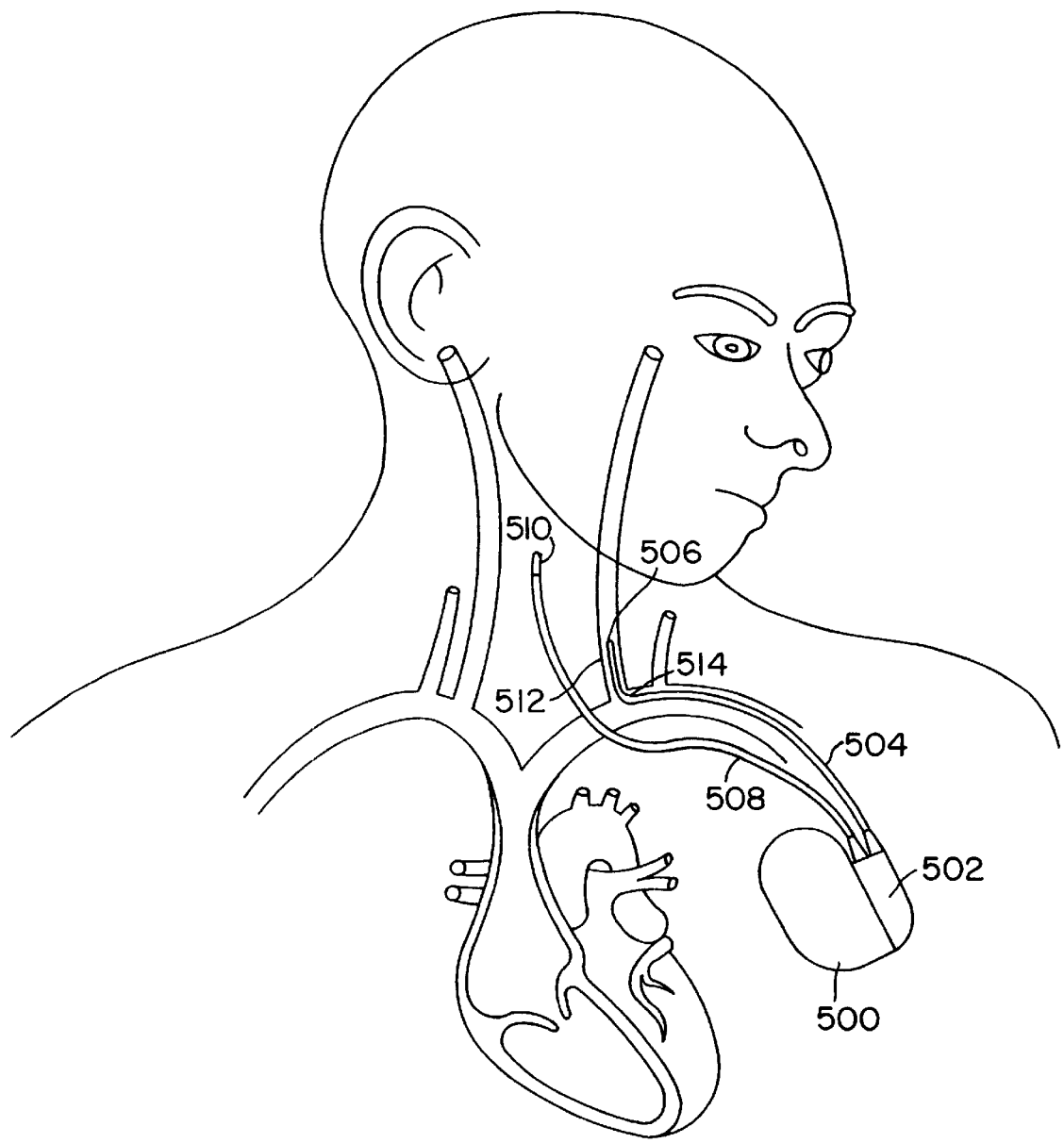
FIG. 18 illustrates an embodiment of the invention employed to stimulate the phrenic nerve in order to provide a diaphragmatic pacemaker.

FIG. 18 illustrates an additional embodiment of the present invention including a pulse generator 500 employed to stimulate the phrenic nerve in order to provide a diaphragmatic pacer. Pacer 500 may correspond generally to that disclosed in U.S. Pat. No. 5,056,519, issued to Vince et al. which employs a signal indicative of the normal respirative function of the right diaphragm to regulate stimulation of the left phrenic nerve to correspondingly stimulate the left diaphragm. A pulse generator 500 is provided with a second lead 508 which carries at its distal tip a temperature sensor 510 which is employed to sense the temperature changes within body tissues resulting from inspiration of outside air through the upper airways. Temperature sensor 510 may be located within the airway to the right diaphragm as described in the Vince patent and employed to regulate stimulus pulses provided to the electrodes on lead 504 so that the left diaphram functions in synchrony with the inspiratory cycle of the right diaphram. Lead 504 may be provided with a preformed bend 514 located an appropriate distance from the electrode array located at the distal end of 506 of the lead to position the electrode array adjacent the phrenic nerve. The lead may be introduced using the procedure described in the above cited Gunderson patent.

Figure 19:
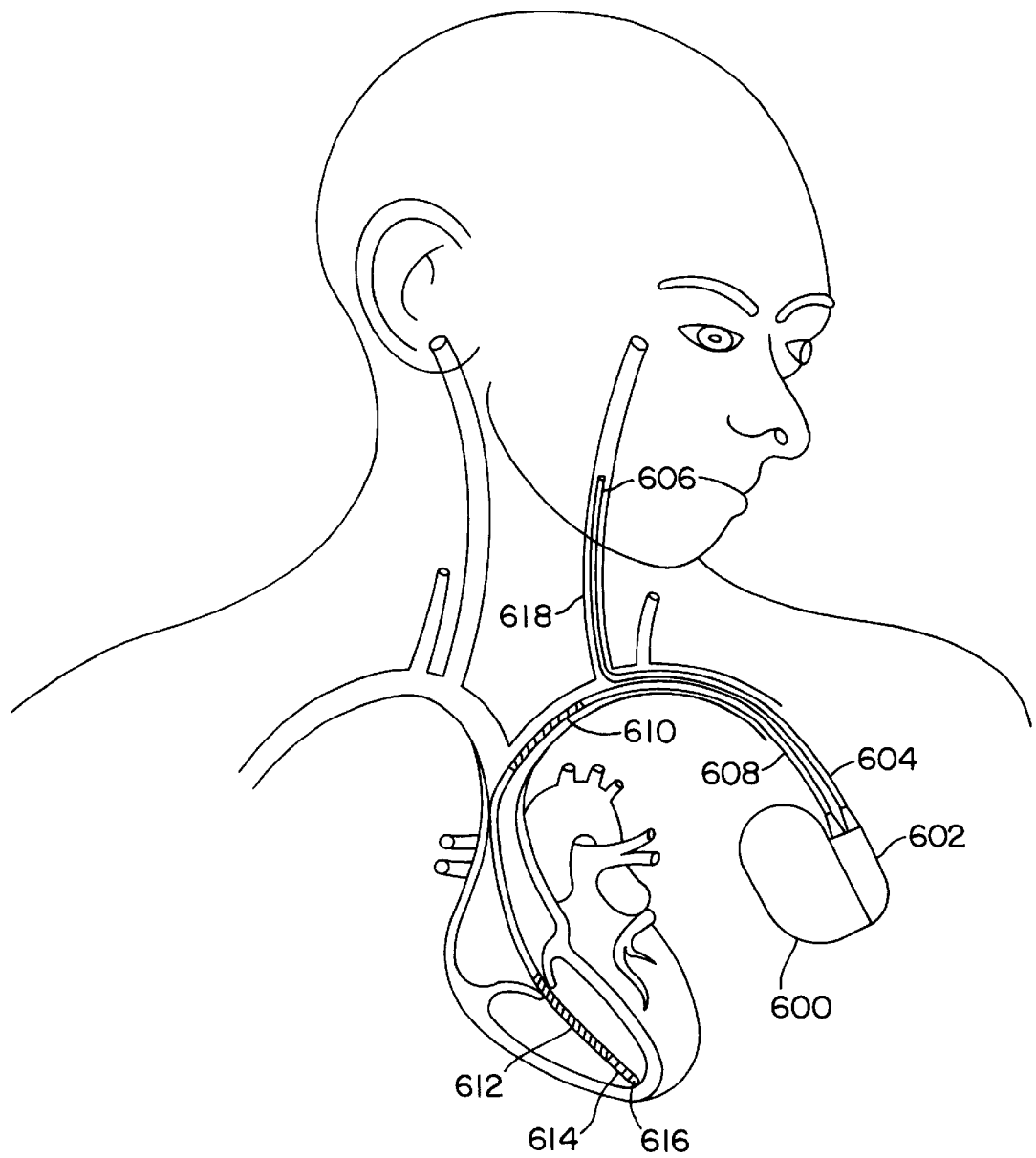
FIG. 19 illustrates an embodiment of the invention as employed in conjunction with an implantable cardioverter defibrillator in which vagal nerve stimulation is employed to treat detected arrhythmias or to prevent arrhythmias.

FIG. 19 illustrates an embodiment of the invention employed in conjunction with an implantable cardioverter/defibrillator 600 which employs vagal nerve stimulation as an adjunct to its array of antitachyarrhythmia therapies including antitachyacardia pacing, cardioversion and defibrillation. Pulse generator 600 may correspond, for example, to the pulse generator illustrated in U.S. Pat. No. 5,014,698 issued to Collins or U.S. Pat. No. 5,243,980 issued to Mehra, both incorporated herein by reference in their entireties.

Pulse generator 600 is provided with an electrical lead 604 which carries adjacent its distal end 606 an array of electrodes as described in conjunction with FIGS. 7–14 above. Electrode lead 604 may correspond to electrode lead 304 illustrated in FIG. 15, with its distal end 606 located within the internal jugular vein in a position appropriate to stimulate the vagal nerve. The pulse generator 600 is also provided with a second electrode lead 608 which carries first and second defibrillation electrodes 610 and 612 and pacing/sensing electrodes 614 and 616 which are employed to sense and pace the ventricle of the patient's heart. The vagal nerve stimulator may be employed in conjunction with delivery of therapies of treatment of arrhythmias or prevention of arrhythmias as described in the above cited Collins et al patent or may be employed as part of a diagnostic regimen as described in the above cited Mehra patent.

The embodiments of the invention illustrated in FIGS. 16–19 above are intended to be exemplary of general types of devices in which the present invention may be employed by transvenously locating an electrode or array of electrodes in a blood vessel adjacent a desired nerve to be stimulated, as discussed above. It should be understood that permanently implanted leads configured and located according to the present invention may be used with a wide variety of implantable electrical devices not specifically illustrated in conjunction with FIGS. 16–19, including implantable drug dispensers, implantable muscle or nerve stimulators, and implantable monitoring systems in which regulation of one or more nervous functions is desired. It should also be understood that in conjunction with such devices, as discussed above, electrodes may be located bi-laterally, and employed to stimulate the same or different nerves, also as discussed above.

Reasonable variation and modification are possible within the spirit of the foregoing specification and drawings without departing from the scope of the invention.

The embodiments for which an exclusive property or privilege is claimed are defined as follows:

1. A method for stimulating desired nerve fibers within a living body, comprising the steps of:

advancing a lead carrying an array of electrodes through the vascular system to a point within a vein adjacent the nerve fibers to be stimulated;

selectively employing electrodes within the array to direct electrical pulses applied to the electrodes to the desired nerve fibers; and delivering electrical pulses to the selectively employed electrodes.

2. A method for stimulating desired nerve fibers within a living body, comprising the steps of:

advancing a lead carrying electrodes through the vascular system to a point within an internal jugular vein adjacent the nerve fibers to be stimulated;

employing electrodes to direct electrical pulses applied to the electrodes to the desired nerve fibers; and delivering electrical pulses to the employed electrodes.

3. A method according to claim 1 or claim 2 wherein said advancing step comprises advancing said lead to position said electrodes adjacent vagus nerve fibers.

4. A method according to claim 1 or claim 2 wherein said advancing step comprises advancing said lead to position said electrodes adjacent hypoglossal nerve fibers.

5. A method according to claim 1 or claim 2 wherein said advancing step comprises advancing said lead to position said electrodes adjacent phrenic nerve fibers.

6. A method according to claim 1 wherein said advancing step comprises advancing said lead to position said electrodes within an azygous vein.

7. A method according to claim 1 wherein said advancing step comprises advancing said lead to position said electrodes within a hemizygous vein.

8. A method according to claim 1 wherein said advancing step comprises advancing said lead to position said electrodes adjacent parasympathetic nerve fibers.

9. A method according to claim 1 wherein said advancing step comprises advancing said lead to position said electrodes adjacent sympathetic nerve fibers.

10. An apparatus for stimulating desired nerve fibers within a living body, comprising:

a transvenous lead carrying an array of electrodes locatable in the vascular system at a point within a vein adjacent the nerve fibers to be stimulated;

switch means for selectively employing electrodes within the array to direct electrical pulses applied to the electrodes to the desired nerve fibers; and pulse generator means for delivering electrical pulses to the selectively employed electrodes.

11. An apparatus according to claim 10 wherein said array is locatable in a patients internal jugular vein adjacent the patient's vagus nerve, and wherein said device further comprises cardiac pacing means for stimulating heartbeats following delivery of pulses to the electrode array.

12. An apparatus according to claim 10 or claim 11 further comprising phrenic nerve stimulation electrodes locatable adjacent the patients phrenic nerve and means for delivering electrical pulses to the phrenic nerve stimulation electrodes in conjunction with delivery of pulses to the electrode array.

* * * * *